United States Patent
Neff (10) Patent No.: US 9,213,928 B2
(45) Date of Patent: Dec. 15, 2015

(54) BAR-CODE ASSIGNMENT SYSTEM FOR MEDICAL AND OTHER USES

(75) Inventor: Robert A. Neff, Penn Valley, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 612 days.

(21) Appl. No.: 13/349,614

(22) Filed: Jan. 13, 2012

(65) Prior Publication Data

US 2013/0098983 A1    Apr. 25, 2013

Related U.S. Application Data

(60) Provisional application No. 61/548,787, filed on Oct. 19, 2011.

(51) Int. Cl.
*G06F 19/00* (2011.01)
*G06K 17/00* (2006.01)

(52) U.S. Cl.
CPC .......... *G06K 17/0025* (2013.01); *G06F 19/327* (2013.01)

(58) Field of Classification Search
USPC ......... 235/494, 375, 376, 462.13, 380; 705/3, 705/16
See application file for complete search history.

(56) References Cited

U.S. PATENT DOCUMENTS

| | | | |
|---|---|---|---|
| 5,696,365 A | 12/1997 | Ukai et al. | |
| 6,283,647 B1 | 9/2001 | Konishi et al. | |
| 7,278,579 B2 | 10/2007 | Loffredo et al. | |
| 7,703,682 B2 | 4/2010 | Kenney | |
| 7,708,198 B2 | 5/2010 | Gangi | |
| 7,712,658 B2 | 5/2010 | Gangi | |
| 7,967,190 B2 | 6/2011 | Hussey | |
| 2002/0132585 A1* | 9/2002 | Palermo et al. | 455/41 |
| 2002/0161708 A1 | 10/2002 | Offer | |
| 2003/0144035 A1* | 7/2003 | Weinblatt et al. | 455/566 |
| 2004/0172300 A1 | 9/2004 | Mihai et al. | |
| 2005/0101844 A1* | 5/2005 | Duckert et al. | 600/300 |
| 2005/0277872 A1 | 12/2005 | Colby et al. | |
| 2006/0106648 A1 | 5/2006 | Esham et al. | |
| 2008/0011825 A1* | 1/2008 | Giordano et al. | 235/380 |
| 2008/0017722 A1 | 1/2008 | Snyder et al. | |
| 2008/0028214 A1 | 1/2008 | Tafoya et al. | |
| 2008/0189170 A1* | 8/2008 | Ramachandra | 705/10 |
| 2008/0198028 A1 | 8/2008 | Watanabe | |
| 2008/0261526 A1* | 10/2008 | Suresh | 455/41.2 |
| 2009/0037515 A1 | 2/2009 | Zapata et al. | |
| 2009/0112072 A1* | 4/2009 | Banet et al. | 600/301 |
| 2010/0001838 A1* | 1/2010 | Miodownik et al. | 340/10.1 |

(Continued)

*Primary Examiner* — Allyson Trail
(74) *Attorney, Agent, or Firm* — Shook, Hardy & Bacon, L.L.P.

(57) ABSTRACT

A bar code generation and processing system for medical and other use comprises at least one repository and a bar code processor. The at least one repository of information includes, identification data of multiple bar code scanners and also associates a bar code displayed in an image associated with an executable application and presented on a device with, the executable application and at least one of, (a) the device and (b) a data destination associated with the application. The bar code processor receives identification data of a bar code scanner and data representing the bar code displayed in the image and uses the information in associating the bar code with the data destination associated with the application and a particular bar code scanner of the multiple bar code scanners. The bar code processor communicates data acquired using the particular bar code scanner to the data destination in response to the association.

21 Claims, 11 Drawing Sheets

(56) References Cited

U.S. PATENT DOCUMENTS

| | | |
|---|---|---|
| 2010/0012715 A1* | 1/2010 | Williams et al. ............... 235/375 |
| 2010/0038417 A1* | 2/2010 | Blankitny ..................... 235/375 |
| 2010/0065634 A1 | 3/2010 | Nakamura |
| 2010/0169120 A1 | 7/2010 | Herbst et al. |
| 2010/0169121 A1 | 7/2010 | Herbst et al. |
| 2010/0219242 A1 | 9/2010 | Gangi |
| 2010/0230485 A1 | 9/2010 | Kenney |
| 2010/0271208 A1* | 10/2010 | Steinmetz et al. ......... 340/572.1 |
| 2011/0072263 A1* | 3/2011 | Bishop et al. ................. 713/168 |
| 2011/0081860 A1* | 4/2011 | Brown et al. ................. 455/41.3 |
| 2011/0101115 A1* | 5/2011 | Rampersad ................... 235/494 |
| 2011/0131061 A1 | 6/2011 | Shain |
| 2011/0210170 A1 | 9/2011 | Arguello |
| 2011/0297747 A1* | 12/2011 | Naumovsky ............. 235/462.13 |
| 2011/0302051 A1 | 12/2011 | Arbatti |
| 2011/0313870 A1* | 12/2011 | Eicher et al. .................... 705/16 |
| 2012/0029303 A1 | 2/2012 | Shaya |
| 2012/0041782 A1 | 2/2012 | Morris |
| 2012/0072536 A1* | 3/2012 | Xu et al. ....................... 709/217 |
| 2012/0179908 A1 | 7/2012 | Duma |
| 2012/0205441 A1* | 8/2012 | Utech et al. .................... 235/376 |
| 2013/0013548 A1* | 1/2013 | Alexander et al. .............. 706/47 |
| 2013/0185092 A1* | 7/2013 | Dubbels et al. .................. 705/2 |
| 2014/0288947 A1* | 9/2014 | Simpson et al. ................. 705/2 |

* cited by examiner

Application Data Tracking 400

| ULID | ULID Type | ULID Description |
|---|---|---|
| 900001 | Text Field | Patient Name Field on Screen Internet Explorer Session ID A91KM188X73 |
| 900002 | Overall Workflow (multi screen) | Workflow on Screen Internet Explorer Session ID A91KM188X73N |
| 900003 | Single Screen | Current Screen for User LNAMEFNAME00 |
| 900004 | Text Box | Text Box 1 on Screen for User LNAMEFNAME00 |
| 900005 | Radio Button Selection | Submit Button 1 on Screen for User LNAMEFNAME00 |
| 900006 | Dropdown Selection | Dropdown Box 2 on Internet Explorer Session ID MA91M47SNROX74VS7 |
| 900006 | Text Field | Drug Name Field on Screen for User LNAMEFNAME00 |
| 900007 | Task id | Task Id of specific task in a workflow process |
| 900008 | Workflow process id | Workflow process identifier |

Server Data Tracking

| Unique Location ID (503) | Unique Location ID Type (505) | Association Barcode (507) | Barcode Wand ID (509) | Application ID (511) |
|---|---|---|---|---|
| 900001 | Text Field | 2000000001 | WAND1 | APL1 |
| 900002 | Overall Workflow (multi screen) | 2000000002 | WAND2 | APL1 |
| 900003 | Single Screen | 2000000003 | WAND3 | APL1 |
| 900004 | Text Box | 2000000004 | WAND4 | APL1 |
| 900005 | Radio Button Selection | 2000000005 | WAND5 | APL1 |
| 900006 | Dropdown Selection | 2000000006 | WAND6 | APL1 |
| 900006 | Text Field | 2000000007 | WAND7 | APL2 |
| 900007 | Task Id of specific task in a workflow process | 2000000008 | WAND7 | APL2 |
| 900008 | Workflow process | 2000000009 | WAND7 | APL2 |

BAR-CODE ASSIGNMENT SYSTEM FOR MEDICAL AND OTHER USES

This is a non-provisional Application of Provisional Application Ser. No. 61/548,787 filed Oct. 19, 2011, by R. A. Neff.

FIELD OF THE INVENTION

This invention concerns a bar code generation and processing system for associating a bar code with a particular bar code scanner and a data destination associated with a particular executable application and communicating data acquired using the particular bar code scanner to the data destination.

BACKGROUND OF THE INVENTION

In known systems, a single barcode is typically directly associated with a barcode data receiving device to support an association between bar code and the device in a computer system, for example. Barcode readers are used with a medical device or other non-PC systems that incorporate embedded software. In industry and healthcare settings, barcode readers are used to capture information from a bar code label and insert it into a software system. This is usually done by using a barcode reader which is connected to a computer system or device. In this case, the data is read from a paper printed barcode label and inserted into an appropriate data field in storage in a system to which the barcode reader is attached.

In known systems a barcode reader typically needs to be physically connected to the system receiving the barcode data. If a wireless barcode reader is deployed, the barcode reader is still required to be matched with a specific device and the device is required to support a driver or connection option for a barcode reader (Serial, USB, or keyboard). In known systems that use a Bluetooth wireless barcode reader, for example, a user needs to use the barcode to scan a particular PC with which to setup a Bluetooth connection. The barcode reader is then associated to that PC. A system according to invention principles addresses these deficiencies and related problems.

SUMMARY OF THE INVENTION

A system enables wireless barcode readers to be used in a processing environment including different devices and different software applications by dynamic assignment of a barcode reader device to a software application using a barcode system server and "association" barcodes including both physical barcodes and dynamically created on-screen software generated barcodes. A bar code generation and processing system for medical and other use comprises at least one repository and a bar code processor. The at least one repository of information includes, identification data of multiple bar code scanners and also associates a bar code displayed in an image associated with an executable application and presented on a device with, the executable application and at least one of, (a) the device and (b) a data destination associated with the application. The bar code processor receives identification data of a bar code scanner and data representing the bar code displayed in the image and uses the information in associating the bar code with the data destination associated with the application and a particular bar code scanner of the multiple bar code scanners. The bar code processor communicates data acquired using the particular bar code scanner to the data destination in response to the association.

DETAILED DESCRIPTION OF THE INVENTION

A system enables wireless barcode readers to be used throughout a software system and on different devices using different software applications by dynamic assignment of a barcode reader device to a software application and elements of the application as well as to associated tasks and processes. The system utilizes a barcode system server and "association" barcodes which might include both physical barcodes and dynamically created on-screen software generated barcodes.

The system enables multiple barcode readers to be deployed throughout an organization. The devices receiving the barcode data are not required to support barcode readers with particular types of driver or connection. This means existing devices may employ firmware modified according to invention principles to take advantage of the barcode system without requiring new hardware or hardware modifications. Also the system enables provision of a barcode reader association for a specific software application or image, not just an entire processing device or PC, for example. Specifically, the system advantageously enables association of a barcode reader with a specific software application, image, or text field allowing greater flexibility than associating the reader to a complete processing device.

Figure 1:
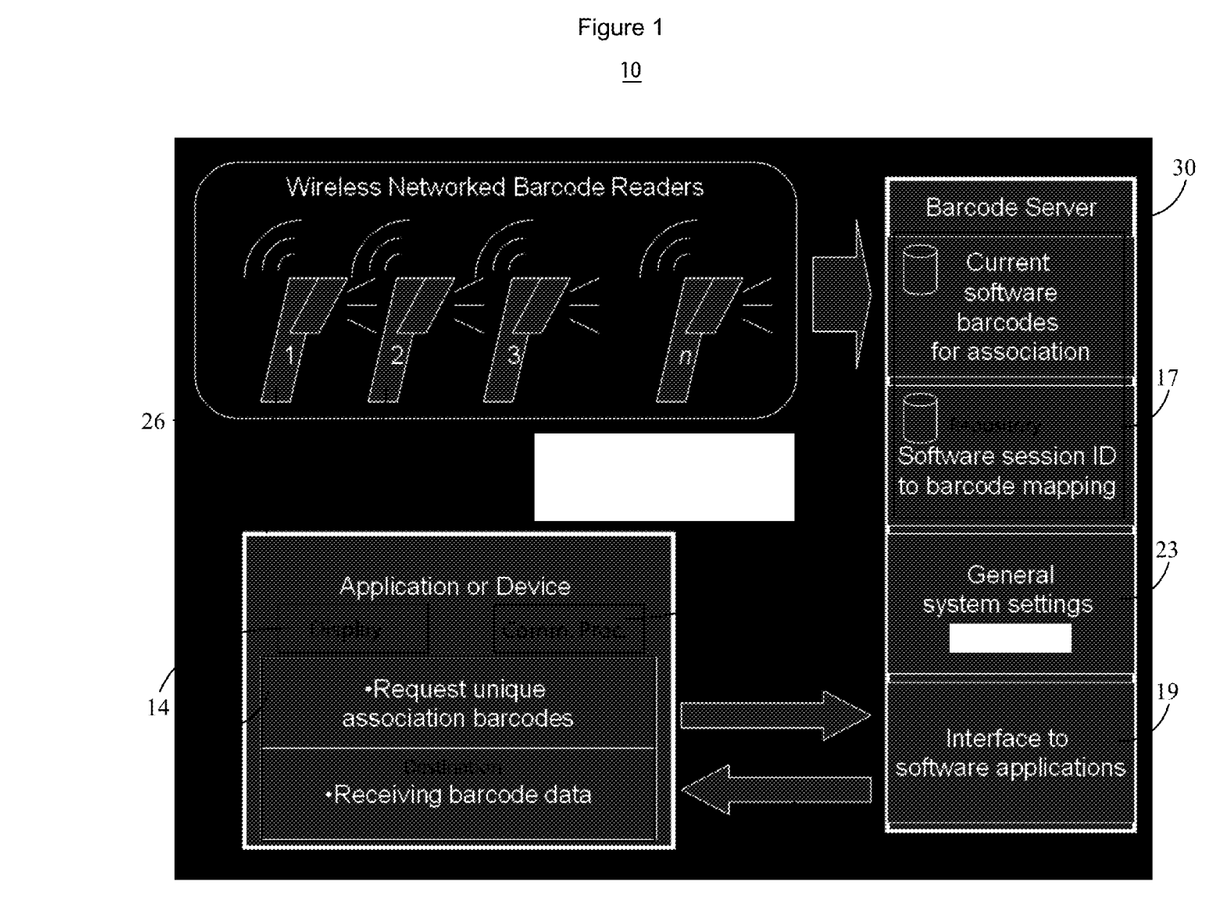
FIG. 1 shows a bar code generation and processing system for medical and other use, according to invention principles.

FIG. 1 shows bar code generation and processing system 10 for medical and other use. System 10 includes one or more processing devices on network 21 (e.g., medical device, infusion pump, workstation, computer or portable devices such as notebooks, Personal Digital Assistants, phones) 12 that individually include a user interface enabling user interaction with a Graphical User Interface (GUI) and display 14 supporting GUI and executable application display image presentation. Processing device 12 executes Application 34 and includes communication processor 16 and the display 14. System 10 also includes bar code scanners 26 including scanners 41 and 42 in wired or wireless communication with server 30 via network 21 or another communication link. Bar code server (processor) 30 includes at least one repository 17, a general system settings function 23 and interface 19 to executable applications (e.g. Application 34).

At least one repository 17 includes identification data of multiple bar code scanners 26 and includes information associating a bar code displayed in an image with executable application 34 and with at least one of, (a) device 12 and (b) a data destination associated with Application 34. The image is associated with Application 34 and is presented on device 12. Bar code processor (server) 30, receives identification data of bar code scanner 41 and data representing the bar code displayed in the image and uses the information in associating the bar code with the data destination associated with application 34 and particular bar code scanner 41 of multiple bar code scanners 26. Bar code processor 30 communicates data acquired using the particular bar code scanner to the data destination in response to the association. Wireless barcode readers 26 operate over a standard wireless network in an enterprise such as a hospital. Processor 30 manages unique onscreen association barcodes and uses repository 17 in tracking mapping between currently associated barcode reader devices and active software sessions. Processor 30 enables addition of wireless barcode readers to the system and change of system configuration. Interface 19 provides an interface that operates over different types of network to send and receive information to software applications which use the barcode system.

Display 14 on device 12 presents an image associated with executable application 34 including a bar code. Communication processor 16 communicates a request for the bar code to a remote system (server 30). Communication processor 16 receives data representing the bar code for presentation in the image from the remote server system 30 in response to the request. The bar code is associated in at least one repository 17 of information, with a data destination associated with application 34 and particular bar code seamier 41 of multiple bar code scanners 26. Processor 16 receives data acquired using particular bar code scanner 41 for incorporation in the data destination in response to bar code scanning of an item with particular bar code scanner 41. Application 34 employs communication processor 16 in requesting from processor 30 unique bar codes associated with data destinations of application 34 and in receiving the barcode data.

System 10 uses barcode reader server 30 to send barcode data to a receiving system or device, such as device 12. An environment has n wireless barcode readers 26 which transmit their data to receiving server 30. Barcodes are generated and presented in an image provided by Application 34 (for example, on a patient header in a healthcare related system). The software generated onscreen barcodes are unique. When a user is ready to scan barcode data for a software application on a terminal or device, the user first scans the barcode on the screen of device 12. This unique barcode is recognized by barcode server 30 as representing a particular instance of a software application user interface image (by a specific session identifier of a webpage, by an identifier associated with the image or by another unique method of recognizing the specific image of images provided by multiple software applications). Data scanned by a barcode reader is transmitted to a software application 34 image to which the reader has been associated. Subsequently, if the image changes, the onscreen barcode is changed or is removed (and the association is discarded). In this case, system 10 requires a changed bar code to be rescanned to re-associate the barcode reader with application 34. A barcode which is scanned by the reader, while the reader is in an unassociated state, is ignored.

A healthcare or other hospital information system using Application 34 employing the barcode system uses a bidirectional interface with the barcode system for transmitting a unique one time barcode being used in an assigned location in an application image or workflow. In addition to transmitting the barcodes which are being displayed, Application 34 transmits to barcode server 30 a location ID (Session ID or other unique identifier) identifying where that unique barcode is being used. Application 34 has a receiving interface for receiving barcode data from the barcode server. This is data which starts with an association barcode and is followed by barcode data. When an association barcode is received by a receiving system, the subsequent associated barcode data is used in the context of the application workflow to which the association barcode belongs.

Figure 2:
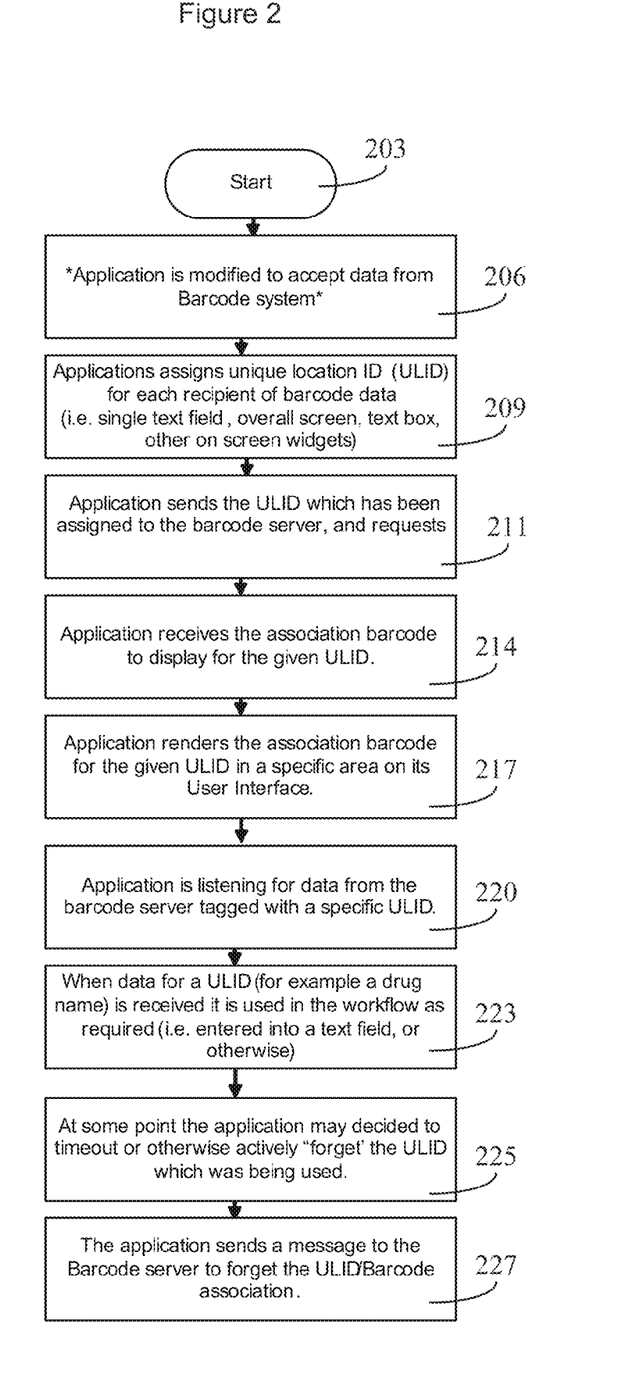
FIG. 2 shows a flowchart of a process for generating and processing bar code data, according to invention principles.
Figure 4:
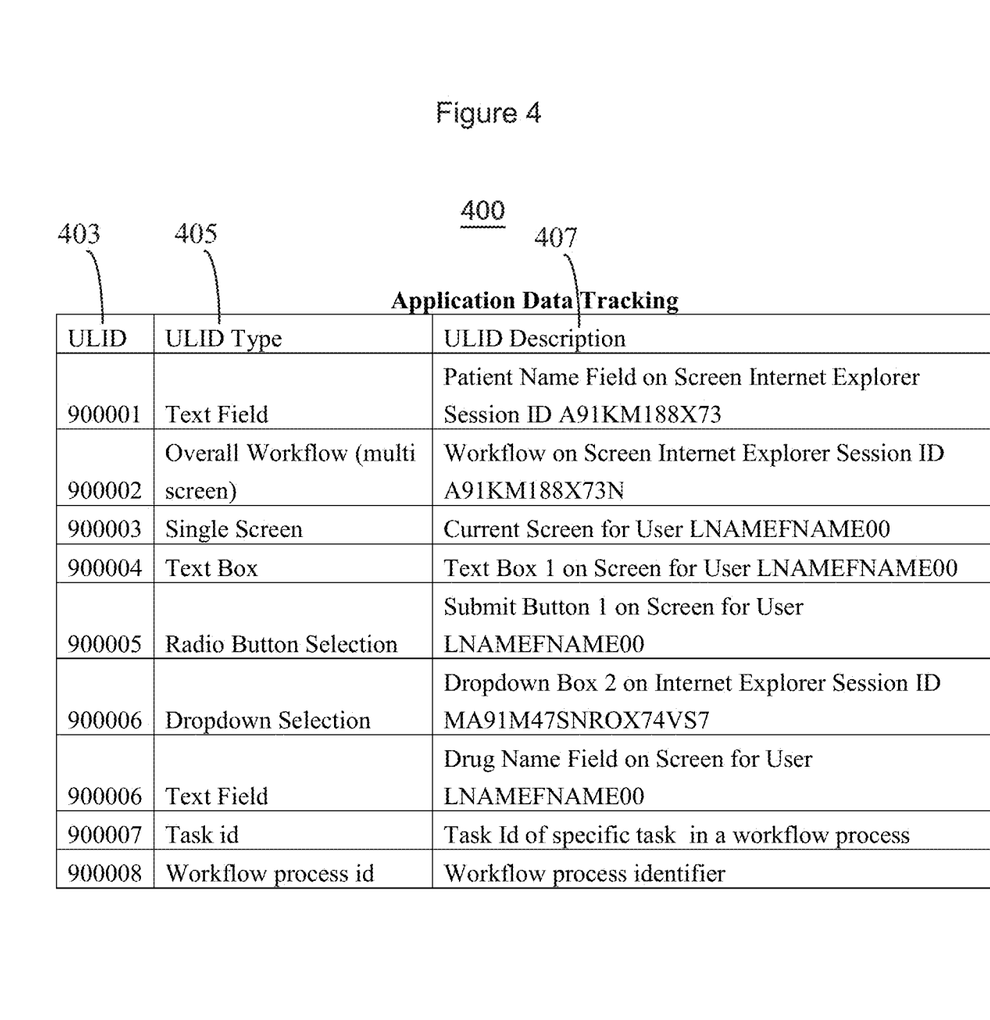
FIG. 4 shows a lookup Table linking a unique location identifier, task identifier or process identifier (ULID) with unique location, task or process type of an associated executable application and with a description, according to invention principles.

FIG. 2 shows a flowchart of a process for generating and processing bar code data. In one embodiment, following the start at step 203, Application 34 that is modified to acquire data from bar code processor 30 in step 206, employs lookup table 400 of FIG. 4 for associating a unique location, task or process type of associated executable Application 34 with a bar code scanner 41 acquired bar code data item. Table 400 of FIG. 4 shows a lookup Table linking a unique location identifier, task identifier or process identifier (ULID) (column 403) with unique location, task or process type (column 405) of an associated executable application and with a description (column 407). A unique location associated with an executable application may comprise, a displayed data field, text field, single display image, displayed button or displayed option list item or a memory location (not shown in Table 400), for example. A unique task associated with an executable application and having a task identifier, may comprise an individual workflow task performed by a user or processing device. A unique workflow process, or executable process associated with an executable application and having a process identifier, may comprise an individual workflow process performed by a user or processing device.

Figure 6:
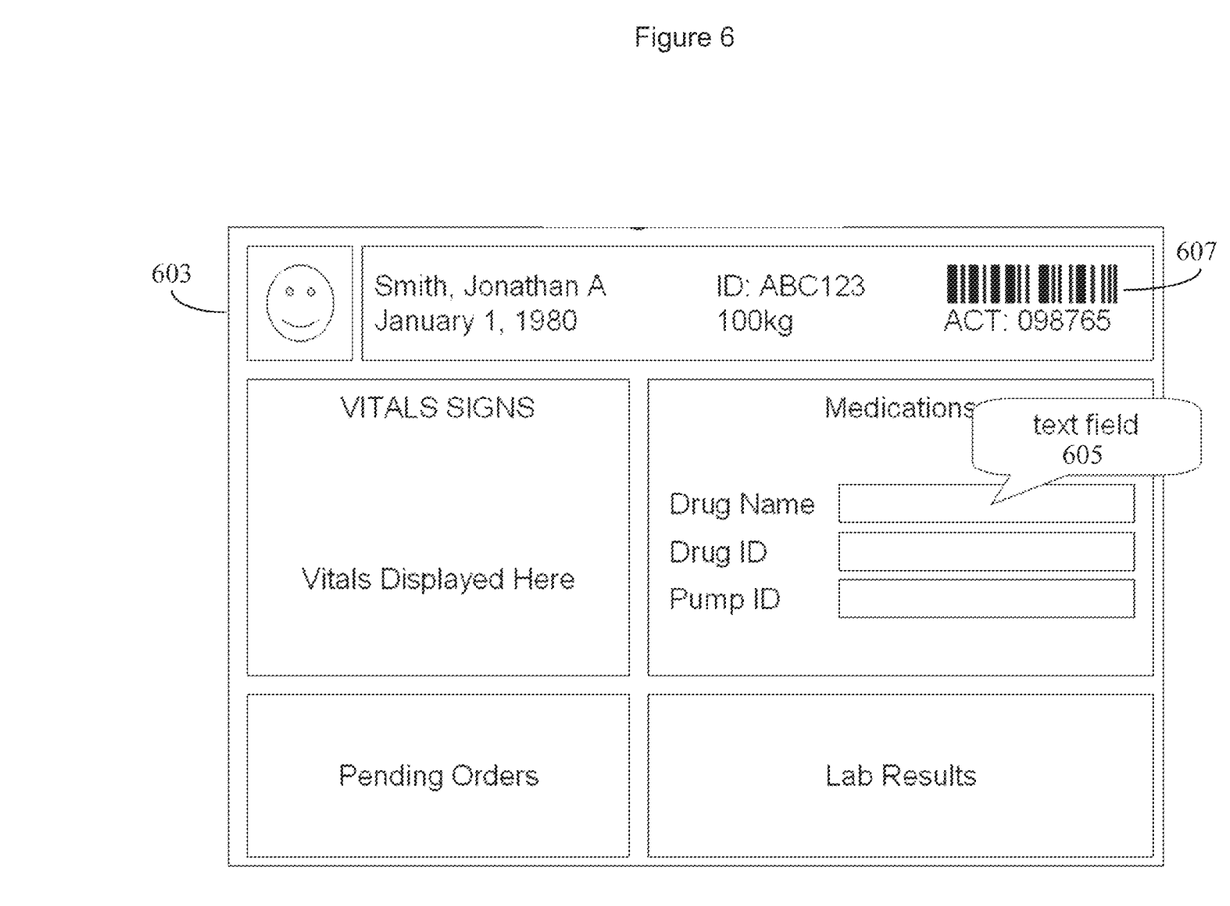
FIG. 6 shows a display image associated with a barcode for an application operation session and a barcode association with a particular text data field in the image, according to invention principles.

FIG. 6 shows display image 603 associated with barcode 607 presented in an Application 34 operation session and the system employs a barcode associated with particular text data field 605 in image 603. In one embodiment, image 603 uses a barcode for a whole computer operation or application operation session and in another embodiment uses a barcode associated with a particular text data field that is not associated with a complete operation session. Application 34 in step 209 (FIG. 2), employs lookup table 400 of FIG. 4 for associating a unique location, task or process type of associated executable Application 34 with a bar code scanner 41 acquired bar code data item. Specifically, Application 34 associates a unique location, drug name text data field 605 associated with executable Application 34 with a bar code scanner 41 acquired bar code data item. In step 211 Application 34 sends a particular unique location identifier (ULID) derived from Table 400 and assigned to text data field 605 to server 30 in a request for display of a bar code associated with data field 605. In step 214 Application 34 receives the requested bar code associated with data field 605 and in step 217 displays the bar code in data field 605 in image 603.

Figure 7:
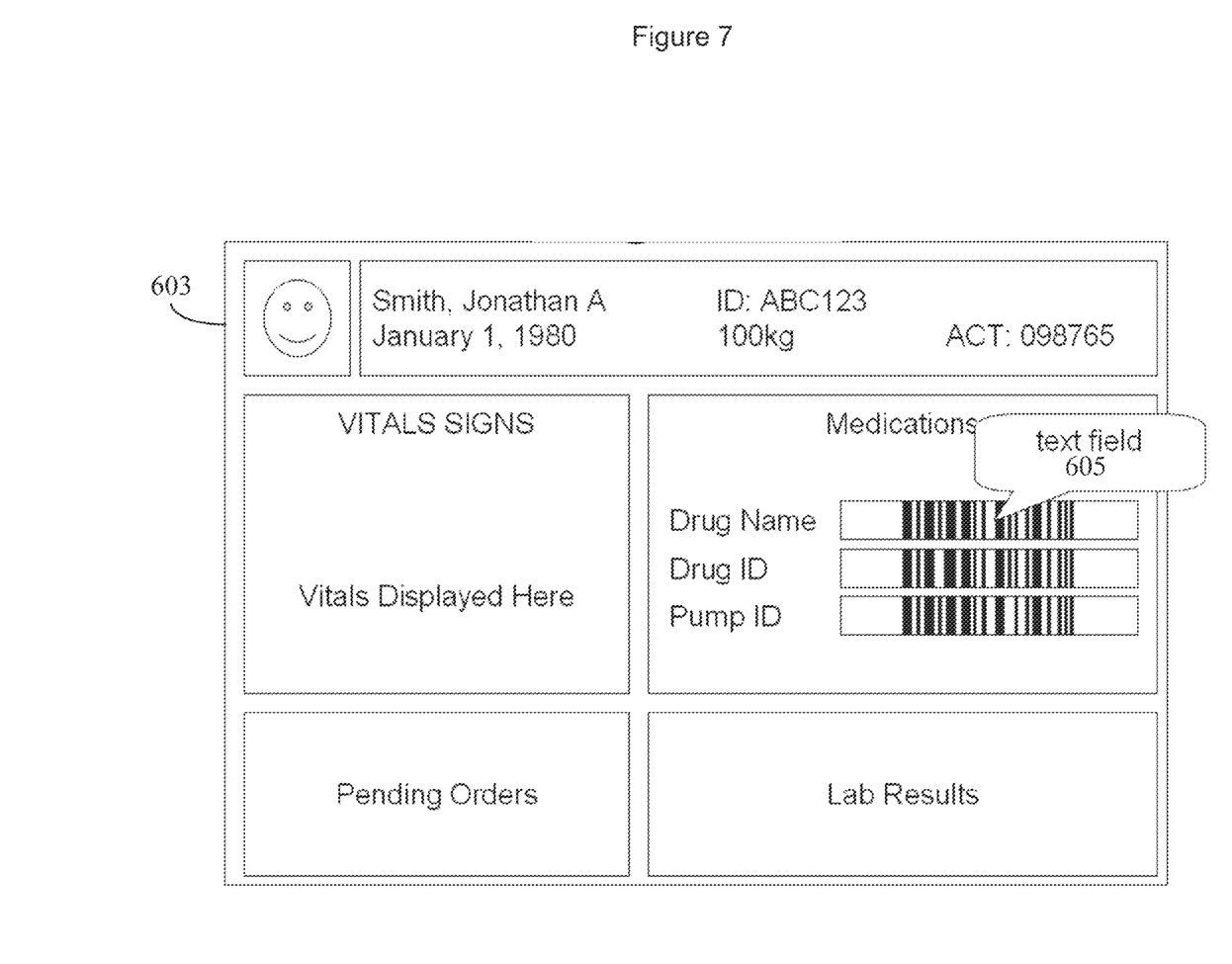
FIG. 7 shows a display image associated with a particular application having particular text data fields associated and populated with particular barcodes, according to invention principles.

Application 34 in step 220 listens for data from server 30 that is tagged with the particular ULID and in response to receiving data representing a drug name, for example, populates data field 605 of image 603 with the drug name in step 223 and uses the drug name in an associated drug administration workflow. In step 225 Application 34 after a predetermined timeout period actively discards the particular ULID being used and disassociates the particular ULID from data field 605. In step 227 Application 34 sends a message to server 30 to initiate discarding the association of the particular ULID with data field 605. The text data field 605 association is used and inactivated substantially when the data barcode is scanned and populated in text data field 605 as shown in FIG. 7. Specifically, FIG. 7 shows display image 603 associated with Application 34 having particular text data field 605 associated and populated with particular barcodes. The barcode system is also usable in embedded systems and in one embodiment a firmware upgrade enables use of the barcode system with a device in associated relevant workflows.

Figure 8:
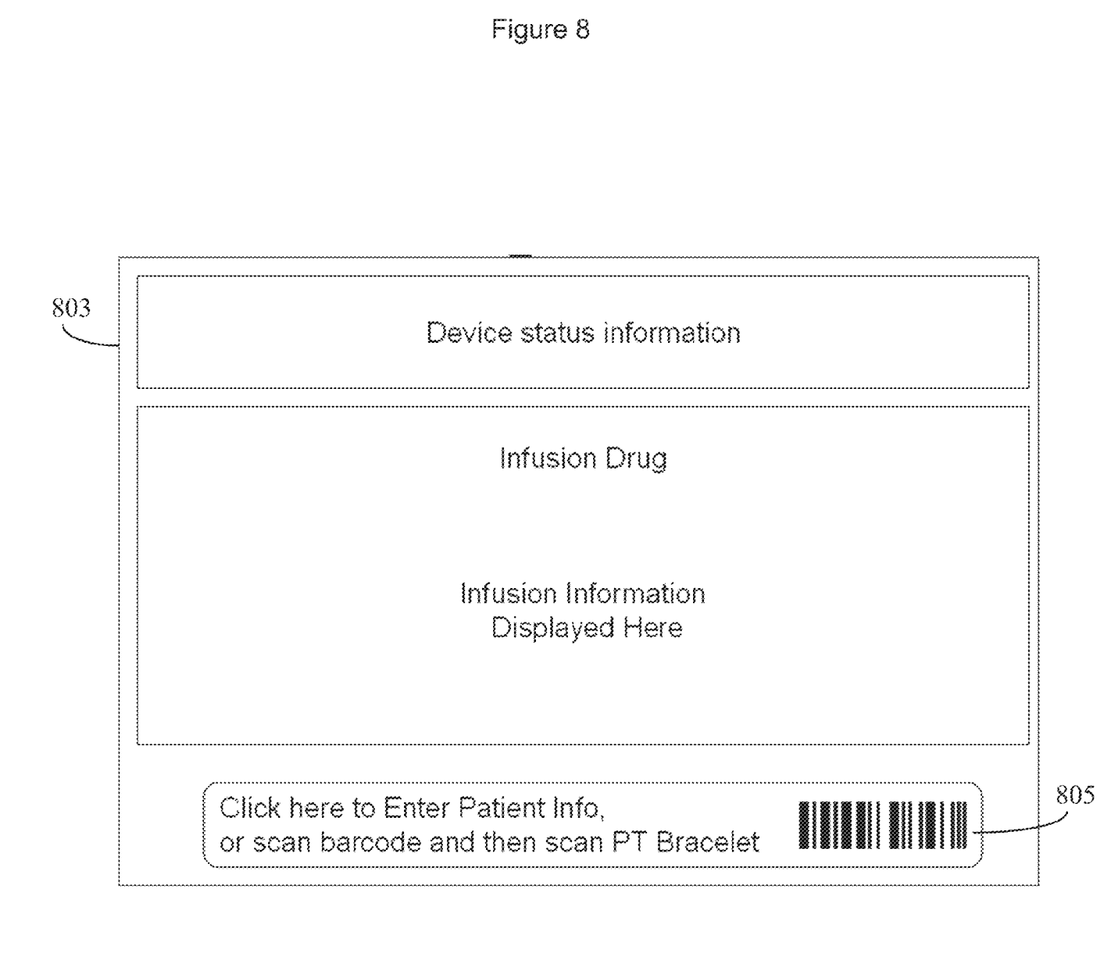
FIG. 8 shows a display image associated with a particular application and infusion pump device having a bar code associated with a particular text data field and infusion pump data item, according to invention principles.
Figure 9:
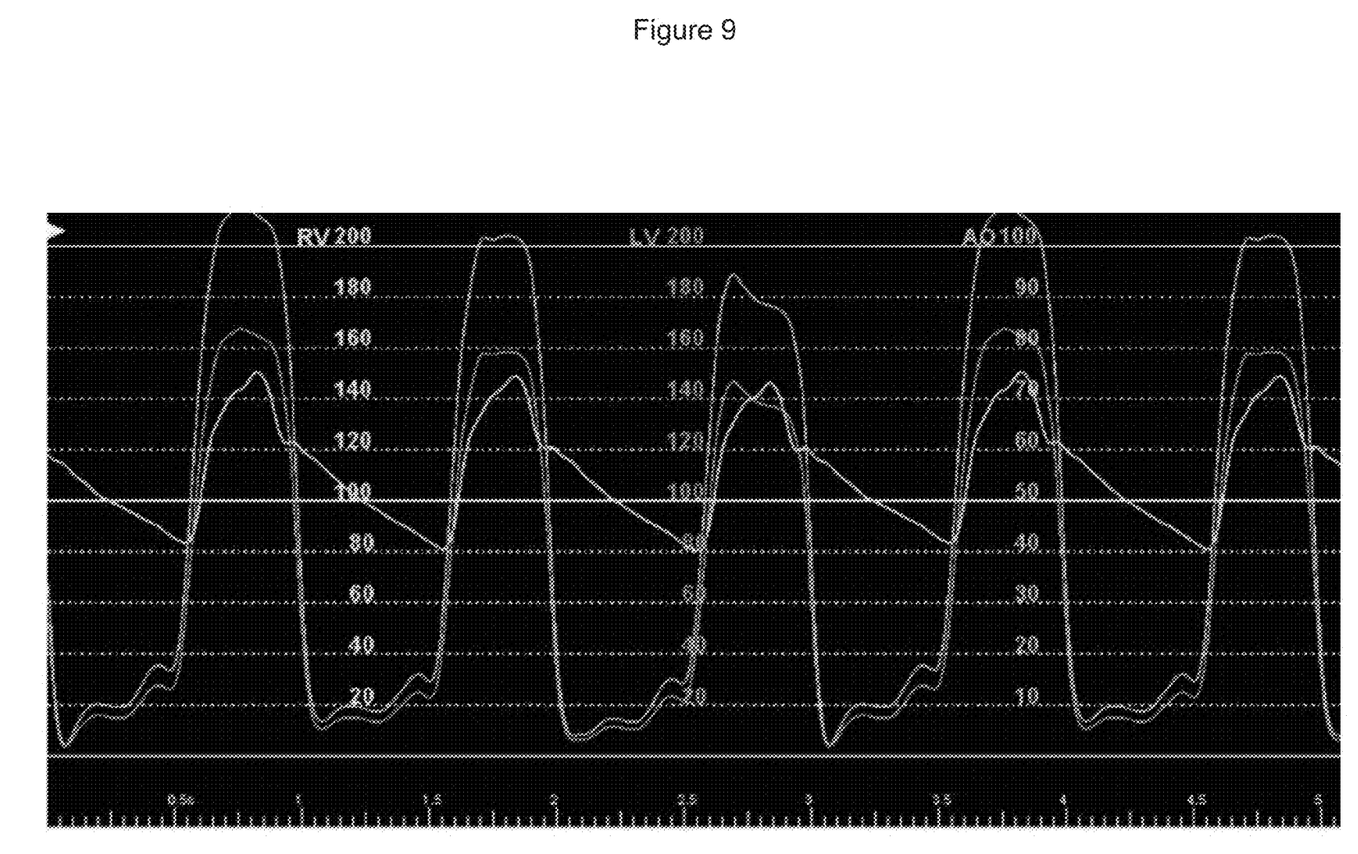
FIG. 9 shows a display of patient monitoring data of a particular patient associated with a patient monitoring device via a bar code association made using a bar code displayed in an image on the patient monitoring device, according to invention principles.

FIG. 8 shows display image 803 associated with a particular application and infusion pump device having a bar code 805 associated with particular text data field and infusion pump data item. In this example, the bar code system is used with an embedded device, an infusion pump. An infusion pump may employ firmware for controlling pump settings and other operational parameters of a device. The pump may also communicate with a pump server which monitors and communicates with multiple pumps. Modified pump firmware displays a barcode in an image on a pump display screen. The barcode is unique and generated by the system for one time use. A clinician, in response to connecting a pump to a patient scans the barcode on the image of the pump (the association barcode) presented on a pump display and scans the barcode on the wristband of the patient (the data barcode). Upon receiving both the association barcode and data barcode scans, the barcode server transmits to the pump gateway, information about the scan. The pump gateway is programmed to send the patient ID information to the pump and set that information in the pump memory. Future data from the pump is transmitted tagged with the correct patient identification information. FIG. 9 shows a display of patient monitoring data of a particular patient associated with a patient monitoring device via a bar code association made using a bar code displayed on an image on the patient monitoring device.

Figure 3:
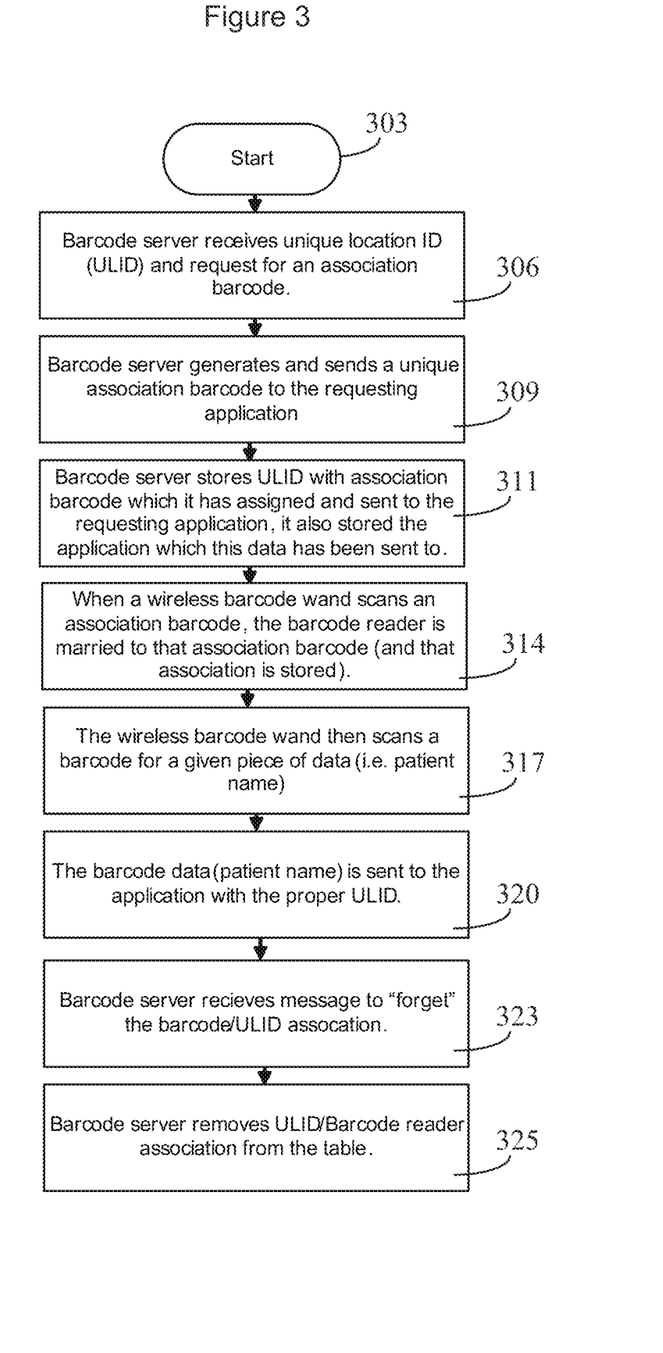
FIG. 3 shows a flowchart of a process for processing bar code data by a remote server, according to invention principles.

FIG. 3 shows a flowchart of a process for processing bar code data by remote processor (server) 30 (FIG. 1). In one embodiment, following the start at step 303, processor 30 interface 19 in step 306 receives a particular unique location identifier (ULID) from Application 34. In step 309, processor 30 generates a unique bar code or retrieves the unique bar code from storage and sends the unique bar code associated with the received ULID to Application 34 via interface 19. Processor 30 in step 311 stores the received ULID in table 500 of FIG. 5 in association with the generated or predetermined associated barcode. Table 5 (FIG. 5) links the received unique location identifier, task identifier or process identifier (ULID) (stored in column 503), with unique location, task or process type (column 505) of an associated executable application, the generated or predetermined associated bar code (column 507) sent to Application 34, bar code scanner identifier (column 509) and with an identifier of the executable application (Application 34, column 511).

Figure 5:
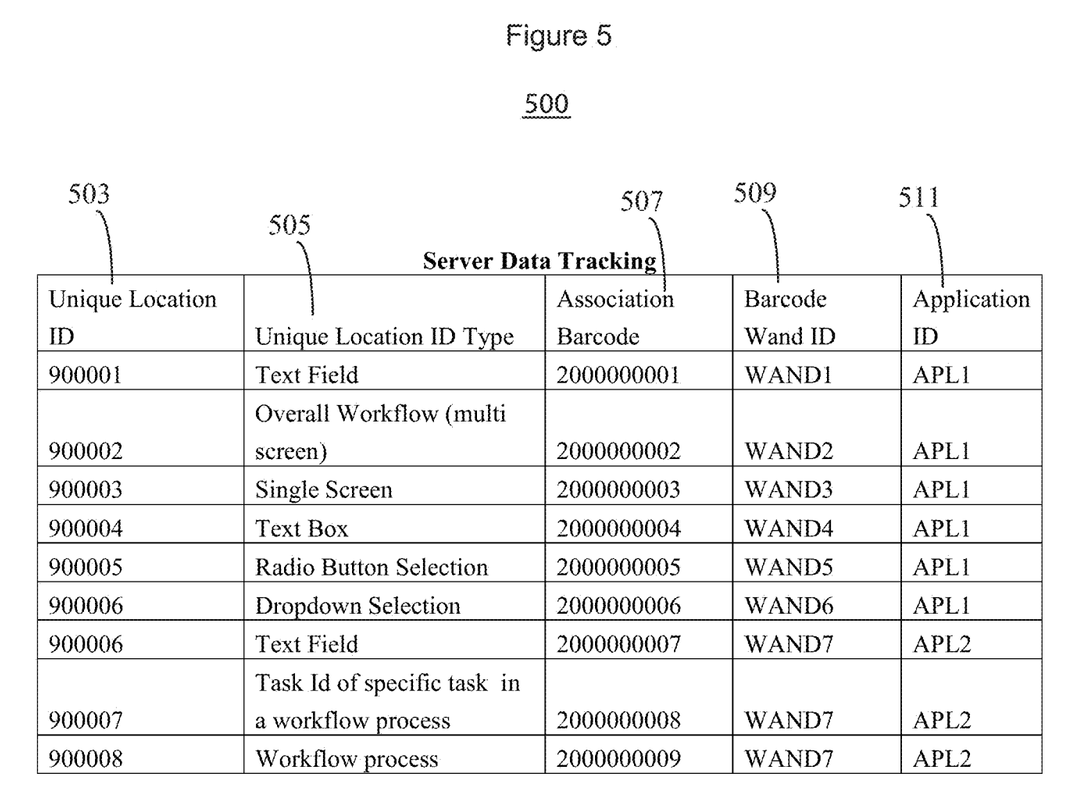
FIG. 5 shows a Table linking a unique location identifier, task identifier or process identifier (ULID) with unique location, task or process type of an associated executable application, associated bar code, bar code scanner identifier and with an identifier of the executable application, according to invention principles.

In step 314, in response to scanner 41 scanning the unique bar code associated with the received ULID sent to Application 34 and displayed in text field 605 (FIG. 6), for example, scanner 41 is associated with the scanned unique bar code by storage of a scanner 41 identifier in Table 500. Scanner 41 is used in step 317, to scan an item of data e.g. a patient name in a wrist band bar code and in step 320 processor 30 sends the patient name to an Application (Application 34) associated with the ULID of the location associated with the unique bar code. In step 323, processor 30 receives a message commanding processor 30 to discard the association of the unique bar code and with the ULID. In one embodiment this message is generated in response to elapse of a timeout period, in another embodiment the message is generated in response to a command by Application 34. Processor 30 in step 325 updates Tables 400 and 500 to remove the association of the unique bar code with the ULID.

Figure 10:
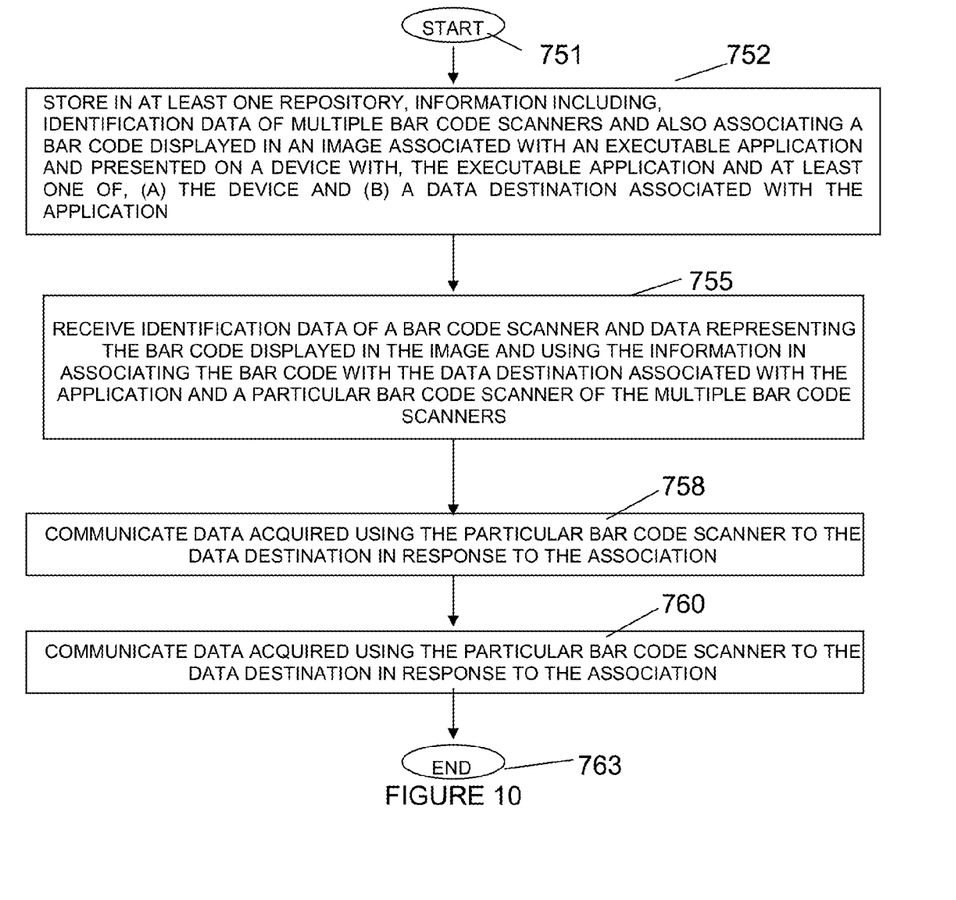
FIG. 10 shows a flowchart of a process employed by a bar code processing system, according to invention principles.

FIG. 10 shows a flowchart of a process employed by a bar code processing system e.g. processor 30 (FIG. 1) for processing bar code (e.g. bar code or a QR (quick response) code) data. Processor 30 in step 752 following the start at step 751, stores in at least one repository 17, information including, identification data of multiple bar code (e.g. wireless) scanners and also data associating a bar code displayed in an image associated with an executable application and presented on a device with, the executable application and at least one of, (a) the device and (b) a data destination (e.g. a data field in a displayed image) associated with the application. In one embodiment, the device is an infusion pump and processor 30 uses the information in associating the bar code with the infusion pump. In another embodiment, the device is an electronic device with a graphical user interface, and processor 30 uses the information in associating the bar code with the electronic device.

The information associates the bar code displayed in the image with elements including, at least one of, (a) a text field, (b) a workflow process, (c) a task identifier of a workflow process, (d) an image associated with the application, (e) a selectable button in the image associated with the application and (f) a value to be entered in an option list in the image associated with the application. Processor 30 uses the information in associating the bar code with at least one of the elements. In step 755, processor 30 receives identification data of a bar code scanner and data representing the bar code displayed in the image and uses the information in associating the bar code with the data destination associated with the application and a particular bar code scanner of the multiple bar code scanners. In one embodiment a bar code scanner is a phone, computer or watch, for example.

Processor 30 in step 758, communicates data acquired using the particular bar code scanner to the data destination in response to the association. Processor 30, receives identification data of a first bar code scanner and data representing the bar code displayed in the image and identification data of a second bar code scanner and data representing the second bar code displayed in the image (or a second image). Processor 30 uses the information in associating the first bar code with a first data destination associated with the application and the first bar code scanner of the multiple bar code scanners and in associating the second bar code with a second data destination associated with the application and the second bar code scanner. Also processor 30 communicates data acquired using the first and second bar code scanners to the respective first and second data destinations in response to the association. In one embodiment, processor 30 dynamically generates the bar code displayed in the image and the bar code is acquired by the application. In step 760, processor 30 discards the association with the dynamically generated bar code displayed in response to completion of use of the bar code. Alternatively, processor 30 discards the association in response detection of completion of a workflow task. The process of FIG. 10 terminates at step 763.

Figure 11:
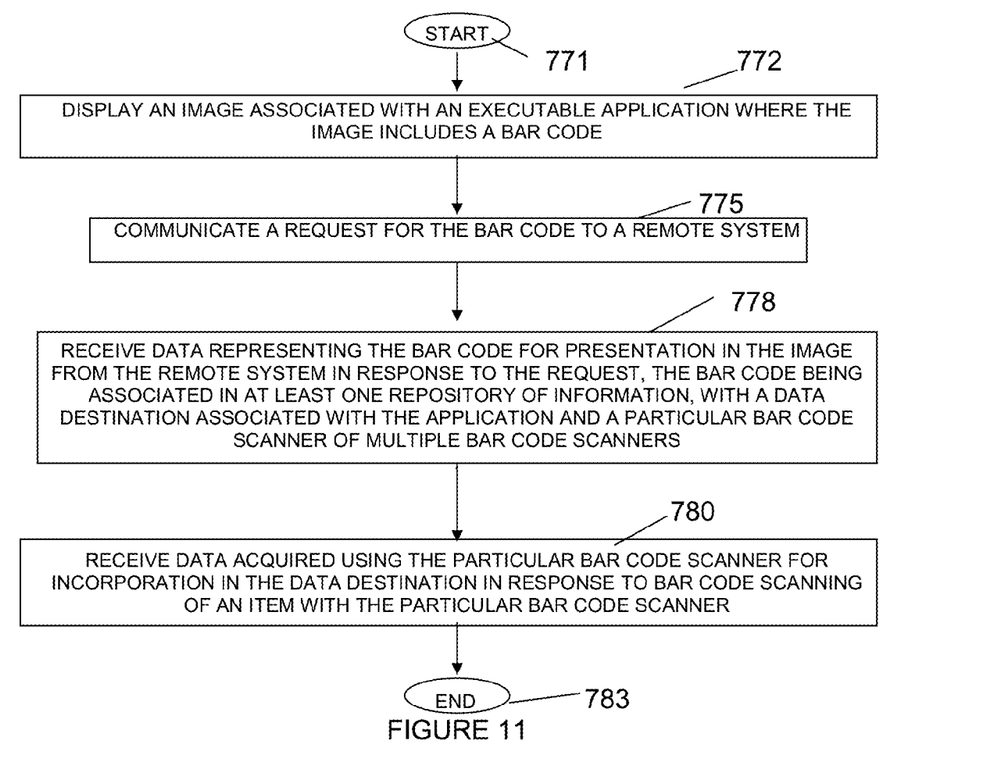
FIG. 11 shows a flowchart of a process employed by a bar code processing application, according to invention principles.

FIG. 11 shows a flowchart of a process employed by a bar code processing Application e.g. Application 34 (FIG. 1) for processing bar code data. Application 34 in step 772 following the start at step 711, displays an image associated with executable Application 34 and the image includes a bar code. In one embodiment, Application 34 operates on a computer in a medical device and the display resides on the medical device (e.g., an infusion pump). In step 775, Application 34 communicates a request for the bar code to a remote system (processor 30). In one embodiment Application 34 includes a communication processor and is within a computer provided on a mobile unit for use in patient rooms in a hospital. Application 34 in step 778, receives data representing the bar code for presentation in the image from the remote system in response to the request. The bar code is associated in at least one repository of information, with a data destination associated with the application and a particular bar code scanner of multiple bar code scanners. The at least on repository of information is within the computer or within the remote system. In step 780, Application 34 receives data acquired using the particular bar code scanner for incorporation in the data destination in response to bar code scanning of an item with the particular bar code scanner. The process of FIG. 11 terminates at step 783.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system associates barcodes which may include both physical barcodes and dynamically created on-screen software generated barcodes with a software application, image, memory location, data field, process, workflow, or text field allowing greater flexibility than associating a bar code reader to a complete device. Further, the processes and applications may, in alternative embodiments, be located on one or more (e.g., distributed) processing devices on a network linking the units of FIG. 1. Any of the functions and steps provided in FIGS. 1-11 may be implemented in hardware, software or a combination of both.

What is claimed is:

1. A bar code generation and processing system, the system comprising:
   at least one repository of information, wherein the at least one repository of information stores identification data for a plurality of bar code scanners and information for associating at least one association bar code with a device and a data destination, wherein the device and the data destination are associated with an executable application; and
   a bar code processor, wherein the barcode processor:
   (1) receives identification data for at least one bar code scanner in the plurality of bar code scanners and the information associating the association bar code with the device and the data destination, wherein the association bar code is displayed in an image provided by the executable application on a display on the device,
   (2) receives data acquired from a data bar code when a scan indication is received from the at least one bar code scanner, wherein the data acquired from the data bar code comprises input data or input parameters for performing one or more computerized operations; and
   (3) communicates the data acquired from the data bar code to the data destination.

2. A system according to claim 1, wherein the data destination is a data field in the image.

3. A system according to claim 1, wherein
   the bar code processor associates the at least one association bar code with elements including, at least one of, (a) a text field, (b) a workflow process, (c) a task identifier of a workflow process,
   the bar code processor uses the information for associating the at least one association bar code with the device and the data destination.

4. A system according to claim 1, wherein
   the bar code processor associates the at least one association bar code with elements including, at least one of, (a) an image associated with the executable application, (b) a selectable button in the image associated with the executable application, (c) a value to be entered in an option list in the image associated with the executable application, and
   the bar code processor uses the information in associating the at least one association bar code with at least one of said elements.

5. A system according to claim 1, wherein
   the device is an infusion pump, and
   the bar code processor associates the infusion pump with the association bar code using the information for associating the at least one association bar code with the device and the data destination.

6. A system according to claim 1, wherein
the device is an electronic device with a graphical user interface, and
the bar code processor associates the electronic device with the association bar code using the information for associating the at least one association bar code with the device and the data destination.

7. A system according to claim 1, wherein the bar code processor
further receives identification data for a second bar code scanner in the plurality of bar code scanners and the information associating a second association bar code with the device and a second data destination, wherein the second association bar code is displayed in the image provided by the executable application on the display on the device; and
communicates data acquired using the second bar code scanner to the second data destination.

8. A system according to claim 1, wherein said bar code processor,
further receives identification data for a second bar code scanner in the plurality of bar code scanners and the information associating a second association bar code with the device and a second data destination, wherein the second association bar code is displayed in a second image provided by the executable application on the display on the device; and
communicates data acquired using the and second bar code scanner to the second data destination.

9. A system according to claim 1, wherein the plurality of bar code scanners are wireless scanners.

10. A system according to claim 1, wherein
the bar code processor dynamically generates the association bar code displayed in the image, and wherein the association bar code is acquired by the application.

11. A system according to claim 10, wherein
the bar code processor discards the the dynamically generated association bar code in response to completion of use of the association bar code.

12. A system according to claim 10, wherein
the bar code processor discards the dynamically generated association bar code in response to detection of completion of a workflow task.

13. A system according to claim 1, wherein
the association bar code comprises a QR (quick response) code; and
the at least one bar code scanner in the plurality of bar code scanners comprises a phone, a computer, or a watch.

14. A bar code processing system comprising:
a display on a device configured to present an image provided by an executable application, wherein the image includes an association bar code, wherein the association bar code is associated with a particular bar code scanner in a plurality of bar code scanners and a data destination associated with the executable application; and
a communication processor, wherein the communication processor
(1) communicates a request for the association bar code to a remote system,
(2) receives data representing the association bar code for presentation in the image, and
(3) receives data acquired by the particular bar code scanner from a data bar code, wherein the data is incorporated in the data destination associated with the executable application, wherein the data acquired from the data bar code comprises input data or input parameters for performing one or more computerized operations.

15. A system according to claim 14, wherein
the communication processor is within a computer provided on a mobile unit for use in patient rooms in a hospital.

16. A system according to claim 14, wherein
the executable application operates on a computer in a medical device and the display resides on the medical device.

17. A system according to claim 16, wherein
the medical device is an infusion pump.

18. A system according to claim 16, wherein the system further comprises:
at least one repository of information, wherein the at least one repository of information stores identification data for the plurality of bar code scanners, and information for associating the association bar code with the medical device and the data destination associated with the executable application, and wherein the at least one repository of information is within the computer.

19. A system according to claim 16, wherein the system further comprises:
at least one repository of information, wherein the at least one repository of information stores identification data for the plurality of bar code scanners, and information for associating the association bar code with the medical device and the data destination associated with the executable application, and wherein the at least one repository of information is within a remote system.

20. A method for bar code processing, the method comprising:
storing, in at least one repository, information including identification data of a plurality of bar code scanners and information associating at least one association bar code with a device and a data destination associated with an executable application, wherein the association barcode is displayed in an image provided by the executable application and presented on the device
receiving identification data of a particular bar code scanner in the plurality of bar code scanners and the association bar code;
receiving data from a data bar code, acquired with the particular bar code scanner; and
communicating, the data acquired from the data bar code to the data destination associated with the executable application, wherein the data acquired from the data bar code comprises input data or input parameters for performing one or more computerized operations.

21. A method for bar code processing the method comprising:
displaying an image provided by an executable application, the image including an association bar code;
communicating a request for the association bar code to a remote system,
receiving data representing the association bar code for presentation in the image from the remote system in response to the request, the association bar code being associated, in at least one repository of information, with a data destination associated with the executable application and a particular bar code scanner of a plurality of bar code scanners; and
receiving data acquired with the particular bar code scanner from a data bar code, for incorporation in the data destination associated with the executable application, wherein the data acquired from the data bar code comprises input data or input parameters for performing one or more computerized operations.

* * * * *